United States Patent [19]

Doblar et al.

[11] 4,397,335

[45] Aug. 9, 1983

[54] ROTARY VALVE ESPECIALLY USEFUL IN A MEDICAL SYSTEM INCLUDING A FLOW-DIRECTED VENOUS CATHETER

[76] Inventors: Dennis D. Doblar, 11520 Grandview Ave., Silver Spring, Md. 20902; John C. Hinkle, 808 Misty Glen La., Dallas, Tex. 75232

[21] Appl. No.: 267,335

[22] Filed: May 26, 1981

[51] Int. Cl.³ .................... F16K 11/085; A61M 5/00
[52] U.S. Cl. ................ 137/625.19; 137/625.47; 604/32
[58] Field of Search .......... 137/625.47, 625.19; 128/214.4, 274, 214 B, 214 R

[56] References Cited

U.S. PATENT DOCUMENTS

| | | | |
|---|---|---|---|
| 3,192,954 | 7/1965 | Gerhold et al. | 137/625.47 X |
| 3,626,938 | 12/1971 | Versaci | 137/625.47 X |
| 3,774,604 | 11/1973 | Danielsson | 128/214.4 |
| 3,834,372 | 9/1974 | Turney | 128/274 X |
| 4,072,146 | 2/1978 | Howes | 128/214.4 X |
| 4,298,026 | 11/1981 | Ambers | 137/625.47 |

FOREIGN PATENT DOCUMENTS

| | | | |
|---|---|---|---|
| 164846 | 11/1905 | Fed. Rep. of Germany | 137/625.47 |
| 36065 | 7/1911 | Fed. Rep. of Germany | 137/625.19 |
| 328844 | 5/1958 | Switzerland | 137/625.47 |

Primary Examiner—Arnold Rosenthal
Attorney, Agent, or Firm—Robbins & Laramie

[57] ABSTRACT

A rotary valve, especially designed for use in medical systems, has an arrangement of passageways in its rotary valve plug and ports in its housing that permit manual manipulation of the valve to switch the medical system from monitoring pulmonary artery pressure to measuring central venous pressure. The system can also be used for cardiac output measurement or for the withdrawal of a mixed venous blood sample. Patient trauma and contamination are avoided.

31 Claims, 31 Drawing Figures

ROTARY VALVE ESPECIALLY USEFUL IN A MEDICAL SYSTEM INCLUDING A FLOW-DIRECTED VENOUS CATHETER

FIELD OF THE INVENTION

This invention is concerned with a rotary valve construction that is generally useful with liquids and gases. More particularly, the valve is especially useful in connection with the administration of medications and intravenous fluids and the measurement of pressures within the body.

BACKGROUND OF THE INVENTION

The use of the flow-directed balloon-tipped pulmonary artery catheter is now well established in clinical practice. It was initially described in 1970 in the important paper by Swan, Ganz et al., "Catheterization of the Heart in Man with Use of a Flow-Directed Balloon-Tipped Catheter", *New England Journal of Medicine (N.E.J.M.)*, 283, 447–451.

The uses for this device range from the management of critically ill patients in the Intensive Care Unit to the monitoring of patients for open-heart surgery, diagnostic cardiac catheterization, and research applications. The device can be used to measure central venous, pulmonary artery and wedge pressures.

The Swan-Ganz catheter equipment and the accessories often employed with it are described in many medical publications, including, for example, the following: *Anaesthesia* 34, 651–656 (1979), "The Swan-Ganz Pulmonary Artery Catheter", and *Anesthesiology* 45, 146–155 (1976), "Hemodynamic Monitoring: Invasive Techniques".

In the operating room and in the intensive care area, the Swan-Ganz, balloon-tipped, pulmonary artery thermodilution catheter is often used for the measurement for intracardiac, intraarterial, and intravenous pressures. Often this use is combined with use for the administration of intravenous fluids and medication. For these purposes, the catheter generally is provided with a thermistor sensor, a distal lumen for pulmonary artery pressure measurement (the lumenal opening generally being at the tip), a proximal lumen generally located about 30 cm from the distal lumen for central venous pressure measurement, and a balloon tip for flow directing. This catheter has become standard for the care of patients with medical histories demanding the careful regulation of fluid balance and for the measurement of cardiopulmonary performance in the operating room and in intensive care.

To use the catheter, it is inserted percutaneously, generally with the assistance of an introducer cannula. The distal lumen is connected with a pressure transducer for monitoring the pulmonary artery pressure. The distal lumen can also be used for mixed venous blood sampling. If so designed, it can be used for the measurement of cardiac output by the thermal dilution principle. It can also be used for the administration of drugs or agents likely to cause phlebitis or which it is desirable to direct in a concentrated form into the heart or great vessels.

The prevention of blood clots in the catheter system is achieved by continuously flushing both lumens with sterile solution. This is usually accomplished by the connection of intravenous fluids to the proximal lumen port and the distal lumen port to the transducer flush system. A schematic diagram illustrating the technique for connecting the transducer appears in the article in *N.E.J.M.*, supra.

In addition, fluid may be injected into the proximal lumen for the determination of cardiac output by the thermal dilution method, and blood may be withdrawn from the distal lumen for the determination of intrapulmonary shunt fraction. Such data as the pressure measurements referred to, cardiac output, intrapulmonary shunt, and body temperature are utilized for the diagnosis and treatment of conditions arising in the operating room and in the intensive care unit.

In current practice, since the central venous pressure measurement is required less frequently than the pulmonary artery pressure measurement from the distal lumen, a single transducer is commonly connected to the distal lumen and a single intravenous solution is connected to the proximal lumen. When the central venous pressure is to be measured, the transducer tubing is disconnected from the distal lumen, both parts being held in the hands, and the intravenous tubing is also disconnected from the proximal lumen, these tubings being placed on the patient's bed. The tubings are then reversed, the intravenous solution being connected to the distal lumen, the transducer being connected to the proximal lumen, and central venous pressure then being measured. The process is reversed to establish the original conditions.

In addition, it is common practice to place additional stopcocks and tubing in the system, to permit the injection of fluid for cardiac output measurement, and for sampling of blood for intrapulmonary shunt determination. These stopcocks are known to be sites of contamination of catheter systems, *Anesthesia and Analgesia*, 55, 141–142 (1979), "Stopcock Contamination". There is always a risk of malpositioning one of the stopcocks, a risk of the entry of air into the system, or of the production of blood clots in the catheter, rendering the catheter non-functional and subjecting the patient to the substantial risks of catheter replacement which include ventricular extrasystoles, heart block, ventricular fibrillation, intracardiac knotting, balloon rupture, thrombus formation and pulmonary infarction, perforation of the pulmonary artery, and infection, *Anaesthesia*, 33, 172–177 (1978), "Hazards of Central Venous Pressure Monitoring". In addition, the catheter should be firmly stitched in place, and all devices attached to it preferably should have locking hubs.

At present, there is no available valve design which permits these measurements, injections or sampling to be made through the operation of a valve, simply, safely, and with the necessary degree of sterility. Accordingly, each time a reversal of the tubings is done, the patient is placed at significant risk for the introduction of bacteria into the catheter and consequent bacteremia, sepsis, and endocarditis. When an array of stopcocks and tubing is used, the arrangement is often baffling, even to its designer, leading often to confusion and sometimes to errors on the part of personnel who must monitor the patient and use the arrangement on a 24 hour per day basis, especially when the designer of the arrangement is not at hand to explain it. Seldom are these arrangements uniform in structure or function, so that each requires study and sometimes experimentation. All of these considerations can generate potentially life-threatening complications for the patient.

In the intensive care area and in the operating room, such procedures may be repeated up to 30 times per day per patient, thus exposing the patient many times to these risks.

SUMMARY OF THE INVENTION

The invention is a rotary valve that is especially designed for certain medical applications. However, the valve has general utility wherever certain types of flexibility are needed in interconnecting different lines of fluid communication.

The rotary valve of the invention comprises a housing having a bore extending partly therethrough. This bore is bounded by a surface of revolution. The housing has a plurality of ports opening into the bore through the side wall of the housing. These ports are disposed in cooperating pairs, each pair of ports being spaced from each other pair of ports.

A valve plug is movably mounted in the bore of the housing for rotary movement therein. This plug is formed with passageways, positioned so that in one orientation of the plug within the housing, the passageways are in communication with the pairs of ports respectively in the housing, to place each port in communication with the other cooperating member in its pair respectively.

In a preferred embodiment of the invention, the pairs of ports are axially spaced of the housing bore, relative to each other, and there are transversely-extending passageways that correspond in number to the number of pairs of ports.

The valve plug is also formed with other passageways therein that are disposed, upon proper orientation of the plug in the housing by rotation thereof, each to be in communication with one port of one pair of ports and with another port from another pair of ports, respectively, to establish communication between these thus-connected ports. Preferably these other passageways are in the form of a plurality of channels in the surface of revolution of the plug. These channels are formed so they can provide communication, respectively, upon proper orientation of the plug, between one port of one pair of ports and a second port from a different pair of ports.

According to another preferred embodiment of the invention, the valve plug is formed with an exposed outer face and with an additional passageway that extends partly axially through the plug from said outer face, and partly transversely through the part of the plug that is within the bore of the housing, opening upon the surface of revolution of the plug. The transverse portion of this passageway is positioned so that upon proper orientation of the plug within the housing, the transverse portion of this passageway is placed in communication with one of said ports in the housing, and the remaining ports are sealed closed by the surface of the plug.

Most preferably, there are two such additional passageways within the plug, the two passageways having different axial extents, so that one of these additional passageways is available for communication with one pair of ports, and the other additional passageway is available for communication with another pair of ports.

For medical applications, all parts are formed to be readily sterilizable, and for quick connection and disconnection of tubing, and an easily detachable cap is provided to close each opening in the exposed outer face of the plug, to facilitate the maintenance of sterile conditions.

In a preferred medical application of this valve, it is used in a medical system that includes: a flow-directed intravenous catheter having a distal lumen and a proximal lumen; a pressure transducer; and an infusion device. The rotary valve is so designed and the system is so connected that when the valve plug is oriented to place the ports in each pair of ports in communication with each other respectively, through the transversely extending passageways in the plug, the ports of one pair of ports are in communication with the proximal lumen and the infusion device respectively, and the ports in the other pair of ports are in communication with the distal lumen and with the pressure transducer, respectively. Upon rotation of the valve plug to make use of the channels in the surface of the plug, rather than the transversely extending passageways therethrough, one channel serves to establish communication between the proximal lumen and the pressure transducer, and the other channel establishes communication between the distal lumen and the infusion device.

It is also possible to orient the plug to establish communication between one port in the exposed outer face of the plug and the proximal lumen, all other ports being sealed closed. This permits the injection of fluid through the port in the exposed outer face of the valve plug, for use in a procedure such as a cardiac output measurement.

In a different orientation of the valve plug, communication can be established between another port in the exposed outer face of the valve plug and the distal lumen, with all other ports being sealed off and out of service. This permits the removal of a blood sample and is useful in a procedure such as the taking of a mixed venous blood sample.

BRIEF DESCRIPTION OF THE DRAWINGS

In the drawings:

FIG. 23 shows the valve, used in the same system, to monitor pulmonary artery pressure;

FIG. 24 indicates use of the valve, in the same medical system, to monitor central venous pressure;

FIG. 25 shows the valve used with a flow-directed balloon-tipped pulmonary artery catheter but without an arterial line, the configuration shown monitoring pulmonary artery pressure;

FIG. 26 indicates use of the valve to monitor central venous pressure in a system with a flow-directed, balloon-tipped pulmonary artery catheter but without an arterial line;

FIG. 27 shows the valve used with a central venous pressure line and an arterial line, but without a flow-directed, balloon-tipped pulmonary artery catheter;

FIG. 28 shows the use of the valve to monitor central venous pressure in the system shown in FIG. 27;

FIG. 29 shows use of the valve in a similar medical system, arranged or oriented to measure cardiac output;

FIG. 30 indicates use of the valve, in a similar medical system, for the extraction of a mixed venous blood sample; and FIG. 31 shows the valve in a configuration to clear blood after extraction of a mixed venous blood sample using the continuous flush device connected to the transducer.

DETAILED DESCRIPTION OF THE INVENTION

Figure 1:
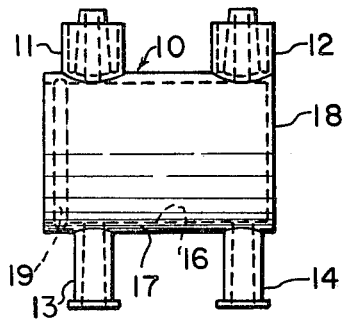
FIG. 1 is a side elevation of the housing for a two channel, six port design for a rotary valve constructed in accordance with one embodiment of the invention.
Figure 2:
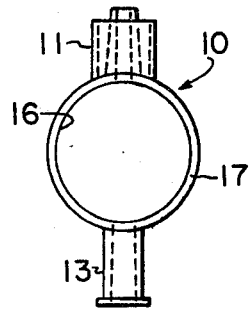
FIG. 2 is an end elevation thereof.
Figure 3:
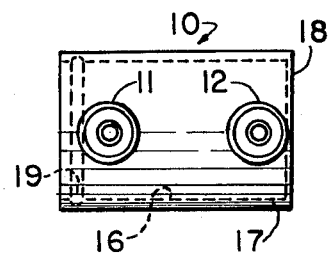
FIG. 3 is a side elevation of the housing rotated through an angle of 90° relative to the position of the housing in FIG. 1.

Referring now in detail to the drawings by numerals of reference, the numeral 10 denotes generally the housing for the rotary valve. This housing is a generally cylindrical body having two ports 11 and 12 respectively, that are arranged in axial alignment. Each of these ports 11 and 12 is equipped as a male, hooded Luer fitting. The housing is also provided with two other ports 13 and 14, respectively, which are in diametric opposition to the first-named ports 11 and 12. The ports 13 and 14 are each formed as female Luer fittings. The Luer-type fittings are standard fittings in use in medical equipment for quick but fluid-tight connection with tubing.

The housing 10 is also formed with a generally cylindrical bore 16, that extends partly through the housing. The bore is thus bonded by a generally cylindrical wall 17 of the housing, and by the closed end 18 of the housing.

The housing wall 17 is formed, just within the open end of the bore 16, with a groove 19, for receiving a resilient retainer ring or an O-ring, as will be described presently.

Turning now specifically to FIGS. 4-7 inclusive, the numeral 20 denotes generally the valve plug. The plug 20 is formed with a generally cylindrical shape. It has a section 21 that is insertable within the housing bore 16, as will presently be described. The plug also has another section 22 that, upon assembly of the two valve parts, projects out of the housing. These two sections 21 and 22 are of different diameters and are separated from each other by a shoulder 24 that, upon assembly, abuts against the end of the housing to limit the travel of the insertable section 21 into the bore of the housing.

In its insertable section 21, the valve plug is formed with a pair of diametrically-extending passageways 25 and 26 respectively, that are spaced from each other axially of the plug, and that are located to be in registry with the pairs of ports in the housing 11 and 13, and 12 and 14, respectively.

Figure 5:
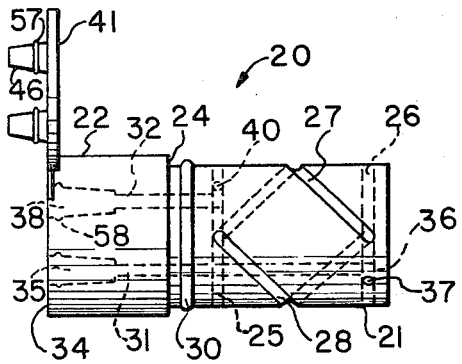
FIG. 5 is a side elevation of the rotary valve plug of FIG. 4, but showing the plug rotated through an angle of 90° relative to the position of the plug in FIG. 4.
Figure 4:
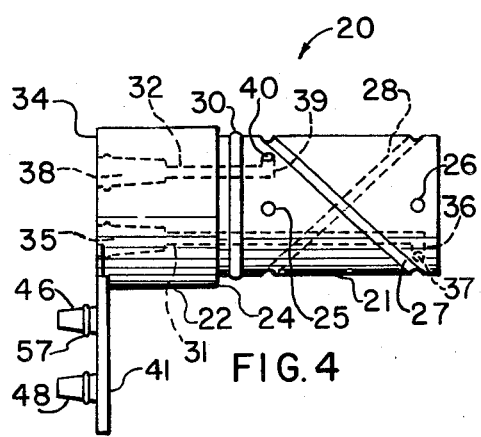
FIG. 4 is a side elevation of a rotary valve plug constructed in accordance with the same preferred embodiment of the invention, and designed for use with the housing shown in FIGS. 1-3.
Figure 6:
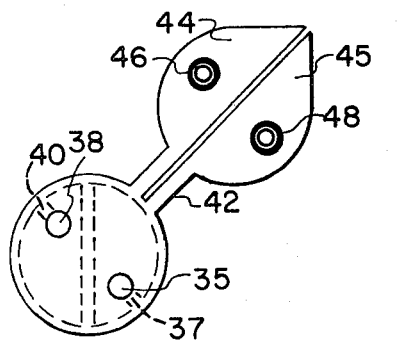
FIG. 6 is an end view of the valve plug, showing a split cap that can be used to close the ports in the end face of the valve plug, the cap in FIG. 6 being shown in its open position.
Figure 7:
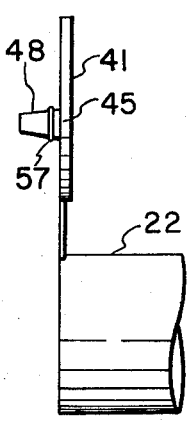
FIG. 7 is a fragmentary side elevation of the end of the valve plug, showing the cap in side elevation, rotated 45° counterclockwise from the position shown in FIG. 6.

The insertable section 21 of the valve plug is also formed to have a generally cylindrical surface designed to confront and engage against the inner surface 16, in fluid-tight fashion. The plug is formed in this surface with a pair of generally helical channels 27 and 28 respectively. These channels have the same pitch, and the midpoint of each is diametrically opposed to the midpoint of the other. Each channel has at one end a generally circular termination that is disposed to be in transverse registry, upon assembly of the valve, with the housing ports 11 and 13, and each has at its opposite end a generally circular termination that is in registry respectively with the ports 12 and 14 of the housing. As best shown in FIGS. 4 and 5, the ends of these channels are angularly spaced from the openings of the two diametrically-extending passageways 25 and 26 respectively, by 90°.

The insertable section 21 of the plug is also formed with a resilient, compressible detent 30, which seats in the groove 19 in the surface of the bore of the housing. Instead of an integral detent 30, an O-ring may be used but is less preferred. The function is to permit snap assembly of the valve.

The valve plug is also formed with a pair of additional passageways 31 and 32 respectively. These passageways extend primarily axially along the length of the plug.

The passageway 31 opens onto the exposed outer face 34 of the plug to provide a port 35. This passageway 31 extends axially of the plug for almost the entire length of the plug, then has a right-angled extension 36 that extends transversely of the plug to open through the cylindrical plug face to provide a port 37. The passageway extension 36 and port 27 have an axis that falls in the same plane as the axis of the transversely extending passageway 26.

Similarly, the additional passageway 32 opens through the outer face 34 of the plug to provide a port 38. This additional passageway 32 extends axially through the body of the plug until it intersects the plane of the axis of the transversely-extending passageway 25. At that point, it has a transverse extension 39 that opens through the cylindrical surface of the plug to provide a port 40.

Figure 8:
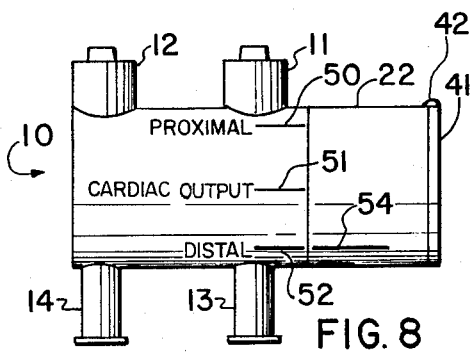
FIG. 8 is a side elevation of a rotary valve assembled from the housing and plug of FIGS. 1-7, showing the indicia that is printed, embossed or otherwise made visible on the surface of the housing for use in a medical system in accordance with one preferred embodiment of the invention, which indicia assist in orienting the plug in the bore of the housing to a position desired for use of the plug in a medical system in accordance with one embodiment of the invention.
Figure 10:
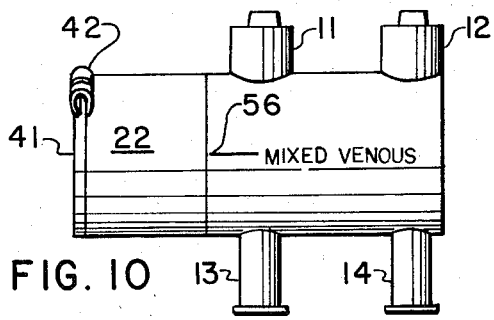
FIG. 10 is a side elevation of the assembly from the side opposite that shown in FIG. 8, showing the indicia that appears on that surface of the housing.

As shown in FIGS. 8 and 10, the valve plug is formed with an integral closure cap that is generally denoted by the numeral 41. This cap is connected to the body of the valve plug through a split hinge 42. The closure cap 41 has two separately operable halves or flaps 44 and 45. These closure flaps are each formed with plugs 46 and 48 respectively, that are shaped for insertion in the ports 35 and 38, to close them. Each plug is formed with a resilient detent ring 57, for seating engagement in a recess 58 that is formed in the surface of each of the ports 35 and 38 respectively.

Figure 9:
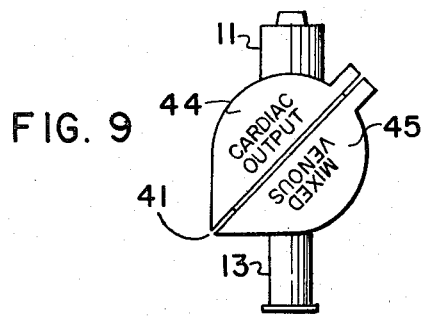
FIG. 9 is an end elevation of the assembly shown in FIG. 8.

Upon insertion of the valve plug into the housing, the assembly shown in FIGS. 8-10 inclusive is obtained, the split closure cap 41 being shown in its closed position.

As shown in FIG. 8, the housing carries thereon three indicator marks, 50, 51, and 52. The indicator mark 50 is accompanied by the legend, "PROXIMAL". The indicator mark 51 is accompanied by the legend, "CARDIAC OUTPUT". The indicator mark 52 is accompanied by the legend, "DISTAL". These three indicator marks are angularly spaced from each other about the periphery of the valve housing as shownn in FIG. 8. Still referring to FIG. 8, the projecting section 22 of the valve plug carries an indicator mark 54. In FIG. 8, the valve plug is oriented with the DISTAL indicator mark 52 and the plug indicator mark 54 in alignment.

As shown in FIG. 10, the other face of the housing is also provided with an indicator mark 56, which is accompanied by the legend "MIXED VENOUS".

Referring to FIG. 9, the flap 44 of the closure cap 41 carries the legend "CARDIAC OUTPUT". The other flap 45 of the closure cap carries the legend, "MIXED VENOUS".

The preferred embodiment of the invention, described above, is well suited for use in connection with a flow-directed, balloon-tipped pulmonary artery catheter, of the kind described in the publication by Swan, Ganz et al., *N.E.J.M.*, supra. Generally such a system will include: a flow-directed intravenous catheter having a distal lumen and a proximal lumen; a pressure transducer with a continuous flush device; and an infusion device.

Figure 11:
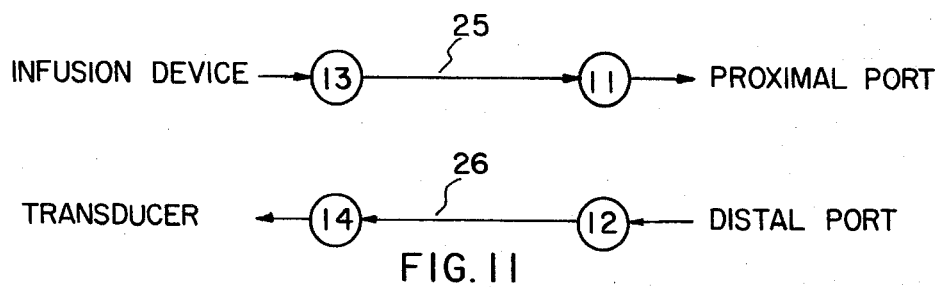
FIG. 11 is a diagram showing the way in which the rotary valve would be used and positioned, normally, when incorporated in a medical system in accordance with one preferred embodiment of the invention, including the valve and lines connecting with other devices, including: a flow-directed intravenous catheter having a distal lumen and a proximaly lumen; a pressure transducer with a continuous flush device, and an infusion device, the diagram indicating that the valve normally is oriented to provide communication between the infusion device and the proximal lumen of the catheter, and also between the pressure transducer and the distal lumen of the catheter.

In such a medical system, the normal orientation of the rotary valve plug is as shown diagrammatically in FIG. 11. The female Luer-type connections (not shown) to the proximal lumen and the distal lumen of the catheter are mated with the male Luer-type connections 11 and 12 of the valve housing. Thus, the proximal lumen of the catheter is connected to the male port 11, and its distal lumen is connected to the male port 12. The pressure transducer is connected, preferably by high pressure flush tubings, to the female Luer-type port 14 of the valve housing. An infusion device, for the maintenance of patency, or for the administration of fluids through the proximal lumen of the catheter, is attached to the female Luer-type port 13 of the valve housing.

In use of the valve, when the indicator line 54 on the projecting section 22 of the valve plug is aligned with the DISTAL datum line 52 on the valve housing (FIG. 8), then the distal lumen of the thermodilution catheter (which is connected to the port 12) communicates with the pressure transducer (which is connected to the port 14) through the transversely-extending passageway 26, as shown in FIG. 11, so that the pulmonary artery pressure can be monitored by the pressure transducer. Still referring to FIG. 11, the infusion device is connected to the port 13 and communicates through the line 25 and port 11 with the proximal lumen of the catheter, so that the patency of the proximal lumen may be maintained. All other pathways are occluded in this orientation.

Figure 12:
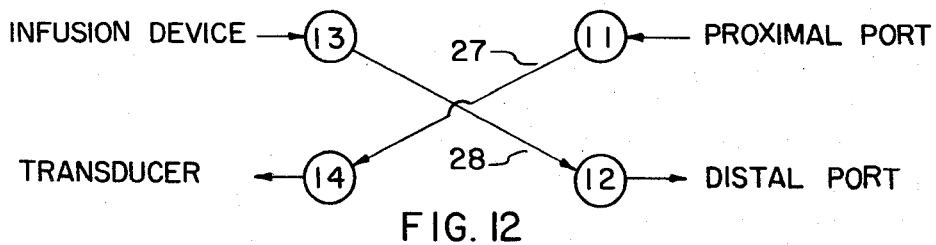
FIG. 12 is a diagramatic representation of the same medical system with the rotary valve in a different position so that communication is provided between the proximal lumen of the catheter and the pressure transducer, and between the distal lumen of the catheter and the infusion device.

Referring now to FIG. 12, when measurements of pressures in the proximal lumen of the catheter are required, such as central venous pressure, the valve plug is rotated within the valve housing 90° from the position shown in FIG. 8, to align the indicator mark 54 on the valve plug with the PROXIMAL mark 50 on the valve housing. In this orientation, the transversely-extending passageways 25 and 26 respectively are occluded. The proximal lumen of the catheter is in communication with the pressure transducer through the port 11, the helical channel 27, and the port 14. Similarly, the infusion device communicates with the distal lumen of the catheter through the port 14, the helical channel 28, and the port 12, and patency in the distal lumen of the catheter is assured. When the measurements are completed, the valve plug can be returned to its initial position shown in FIG. 8, so that the distal lumen (pulmonary artery pressure) is returned to communication with the pressure transducer as shown in FIG. 11.

When it is desired to perform a cardiac output measurement, the valve plug is rotated 45° within the housing from the position shown in FIG. 8, to align the indicator mark 54 on the valve plug with the CARDIAC OUTPUT indicator mark 51 on the housing. At this orientation, the transversely extending passageways 25 and 26 are occluded; the helical channels 27 and 28 are occluded; and the port 40 of the extension 39 of the axially-extending passageway 32 in the valve plug is aligned with the port 11 of the housing and, thus, the axially-extending passageway 32 is in communication with the proximal lumen of the catheter. By lifting off the closure flap 44, a syringe may be inserted in the port 38 in the outer face 34 of the plug, and fluid may be injected into the axially extending passageway 32 for passage to the proximal lumen of the catheter.

When the injection has been completed, the cap 44 and its plug 46 may be cleaned and then the closure plug 46 may be snapped back into the port 38 to seal off the passageway 32. After the cardiac output measurement procedure has been completed, the valve plug may be rotated in the housing to return it to the position shown in FIGS. 8 and 11.

Figure 14:
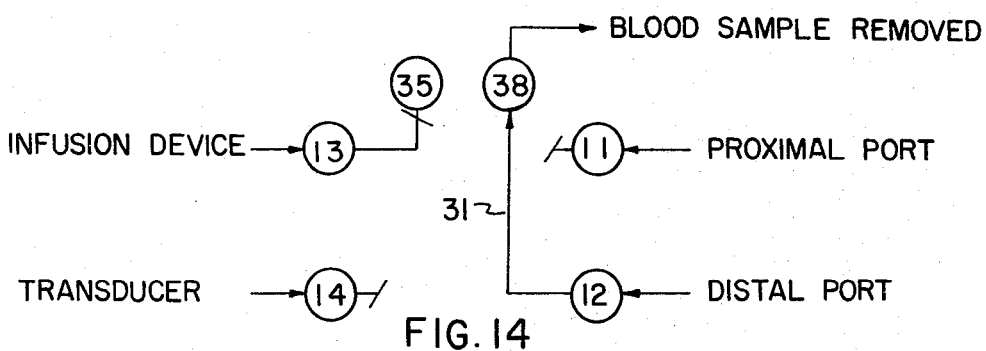
FIG. 14 is a diagramatic representation of the same medical system, with the rotary valve in still another position, in which communication is established between another port in the exposed end face of the rotary plug and the distal lumen of the catheter, and all other ports are inoperative.
Figure 15:
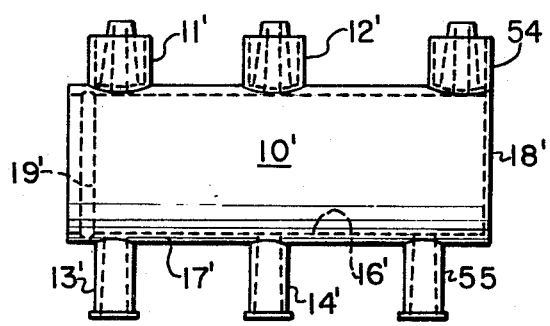
FIG. 15 is a side elevation of a housing designed for a different preferred embodiment of the invention wherein the valve is provided with three channels and eight ports.
Figure 16:
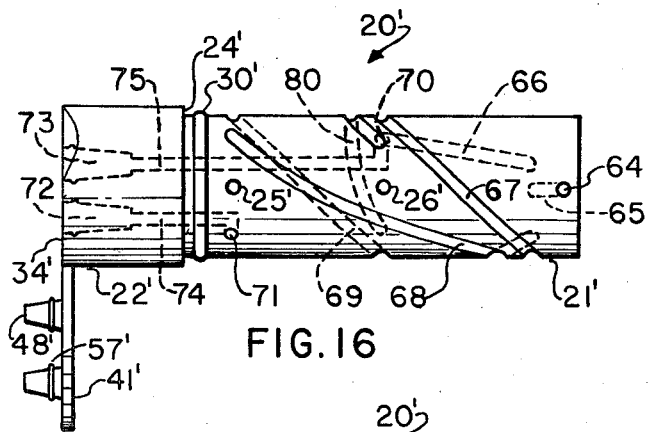
FIG. 16 is a side elevation of a rotary plug for this valve.
Figure 18:
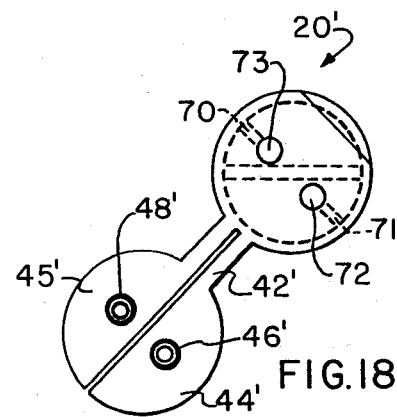
FIG. 18 is an end view of the plug of FIG. 16, showing the integral end cap with its closure flaps.
Figure 17:
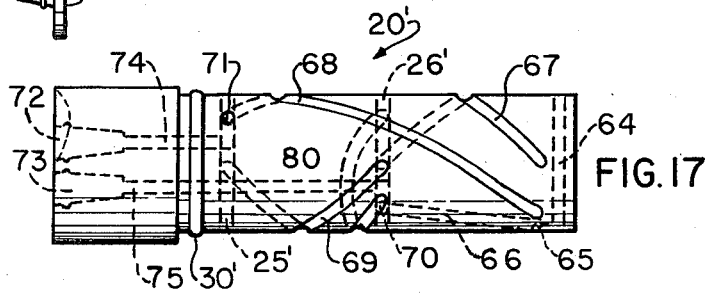
FIG. 17 is another side elevation thereof, but rotated 90° from the orientation of the plug in the side elevation of FIG. 16 (the end cap being omitted for simplicity)

Referring now to FIG. 14, when it is desired to obtain a mixed venous blood sample from the distal lumen of the catheter, the valve plug is rotated until the mark 54 is aligned with the MIXED VENOUS line 56 (FIG. 10). In this orientation of the valve plug, the transversely extending passageways 25 and 26 are occluded. The helical channels 27 and 28 are occluded; and the port 37 in the cylindrical surface of the insertable section 21 of the valve plug is aligned with the port 12 in the housing, thus placing the axially extending passageway 31 in communication through the port 12 with the distal lumen of the catheter. By lifting off the closure flap 45, a syringe may be inserted through the port 35, to permit removal of a blood sample.

Figure 13:
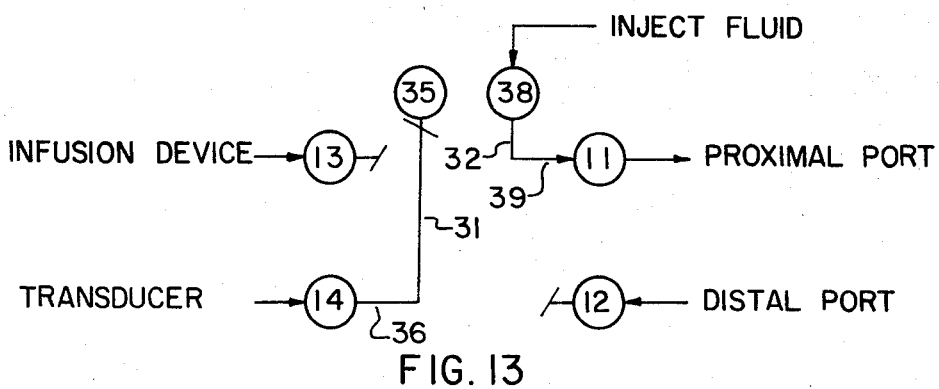
FIG. 13 is a diagramatic representation of the same medical system with the rotary valve in still a different position, in which one port in the exposed end face of the rotary plug is in communication with the proximal lumen of the catheter and all of the other ports are inoperative.

Because blood remains in the axially-extending passageway 31 after the blood sample has been removed, a flushing operation is necessary. To accomplish this, the valve plug is rotated through 180° until the indicator mark 54 is aligned with the CARDIAC OUTPUT mark 51. In this position, the port 37, that opens in the cylindrical surface of the valve plug, is aligned with the port 14 in the housing, the axially-extending passageway 31 may be flushed using the transducer flush, the line of communication being that shown in FIG. 13. The closure flap 45 should then be cleansed, and the closure plug 48 can then be inserted in the port 35 again. The valve plug is then rotated to return it to the position shown in FIG. 8.

Advantages

A valve constructed in accordance with the foregoing preferred embodiment of the invention has many advantages for use in medical applications. It can be fabricated from a synthetic plastic, and the cost is sufficiently low so that it is disposable. It is also readily sterilizable.

The valve is manually operated. It can be formed, as illustrated in the drawings, with male and female Luer and Linden fittings, which are in standard use on current medical pressure monitoring and fluid administration lines.

Another important advantage of the valve is that it provides the capability of switching to fluid lines along simple, direct, small volume pathways to eliminate the potential for the formation of air bubbles and to minimize abrupt directional changes. The presence of air bubbles in a catheter line can significantly alter frequency response and pressure accuracy. Reference, *Anesth.* 53, 498–504 (1980), "The Dynamic Responses of Liquid-Filled Catheter Systems for Direct Measurement of Blood Pressure". If the valve housing is constructed of a clear, transparent synthetic plastic, visual inspection can be used to detect the presence of air bubbles in the less direct pathways. Severe direction changes can adversely affect and alter frequency response.

Particularly when compared to present techniques, use of the valve simplifies procedures, increases reliability, and greatly minimizes the potential for contamination. Use of the valve decreases the time required to perform volume-flow measurements, pressure measurements, fluid injections, and fluid samplings. In addition, the valve provides an injection port through which liquid can be injected into a low volume pathway which is in communication with an easily selected outlet port. The visual signals on the valve itself minimize the opportunity for error. The occlusion of ports not in use, through proper orientation of the valve, protects the transducer and insures the use of the correct volume for injection when cardiac output is measured.

The valve also provides a blood sampling port that communicates with a low volume pathway. This low volume pathway in turn is in communication with the appropriate port in only one orientation of the valve plug in its housing.

The separate flaps on the closure cap occlude and protect the injection and blood sampling ports. Since they may be molded with and integral with the valve plug, their presence in the device greatly minimizes the potential for contamination.

The valve also provides the ability to flush residual blood from the blood sampling port using the transducer flush, thus preventing clotting and subsequent occlusion of the port. While flushing, all uninvolved ports in the valve are occluded.

While offering many advantages, the structure of the valve involves the use of only two parts. Preferably, the housing is formed from a clear synthetic resin, and the valve plug is opaque, formed of a resilient, compressible material with an integral closure cap. If the ring 30 is made integral with the valve plug, the use of an O-ring being eliminated, sterilization is facilitated.

Three Channel, Eight Port Valves

There are situations in the operating room and in the surgical intensive care setting where it is desirable to monitor a thermodilution catheter, with its proximal and distal ports, as well as an arterial line for blood pressure, utilizing one or more pressure transducers. The basic principles of the present invention, discussed above in connection with one embodiment of the invention wherein the rotary valve has two channels and six ports, can be incorporated in another preferred embodiment of the invention in which the valve has three channels and eight ports.

Referring now in detail to FIGS. 15–21 by numerals of reference, like numerals, primed, have been applied to parts of this valve that are essentially similar to the valve shown in FIGS. 1 through 10 inclusive. Structural descriptions that are obvious from the earlier drawings and description are not repeated.

The housing 10' is provided with an additional male Luer-type port 54, and an additional female Luer-type port 55. These two ports are not diametrically opposed as is the case with the other ports of this valve housing.

The insertable section 21' of the valve plug 20' is formed with a pair of diametrically-extending passageways 25' and 26' respectively. It is also formed in its generally cylindrical surface with three primary helical channels. A first helical channel 67 is disposed so that, upon proper orientation of the plug within the housing, it can provide communication between the ports 12' and 55 of the housing. A second helical channel 68 is formed so that upon proper orientation of the plug in the housing, it provides communication between the ports 11' and 55 respectively. The third helical channel 69 is so formed that upon proper orientation of the plug in the housing, it provides communication between the ports 11' and 14'.

The insertable section 21' of the valve plug is also formed with a diametrically extending, passageway 64 (FIGS. 16 and 17), which in the assembled valve, has an axis that is aligned with the axis of the port 54. The plug section 21' is also formed in its cylindrical face with a short channel 65 that communicates with the passageway 64, and that, upon proper orientation of the plug, provides communication between the port 55 and the passageway 64, to permit communication of the passageway 64 with the port 54.

The plug section 21' is also formed with a helical channel 66 that is formed so that upon proper orientation of the plug in the housing, the end of the channel 66 furthest inserted in the housing communicates with the port 55. The other end of the channel 66 communicates with a port 70 to be described presently.

The valve plug is also formed with a pair of axially extending passageways 74 and 75. The passageway 74 opens through a port 72 in the outer face 34' of the plug. At its other end, the passageway 74 has a short, transversely extending section that opens through a port 71 that is transversely aligned to be in the same plane as the axis of the ports 11' and 13'. The passageway 75 opens through the outer face 34' of the plug through a port 73, and at its other end has a short transverse extension that opens on the cylindrical surface of the plug to provide the port 70.

The insertable section 21' of the valve plug is also formed with a curved channel 80 (FIG. 17) in its generally cylindrical surface. This channel 80 is formed so that upon proper orientation of the valve plug, it provides communication between the port 14' and the port 12'.

Figure 19:
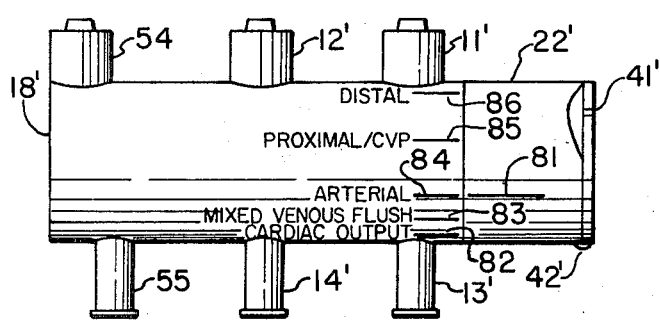
FIG. 19 is a side elevation of a valve assembled from the housing and plug of FIGS. 15 thru 18 inclusive, the end cap being in its closed position, the housing surface shown being opposite to that shown in FIG. 15, and showing the indicia on the housing and on the plug that assist in orienting the plug correctly for operation in a medical system in accordance with a preferred embodiment of the invention.
Figure 20:
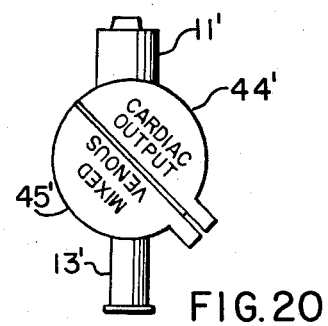
FIG. 20 is an end view of the assembled valve, showing the indicia on the two closure flaps of the end cap.
Figure 21:
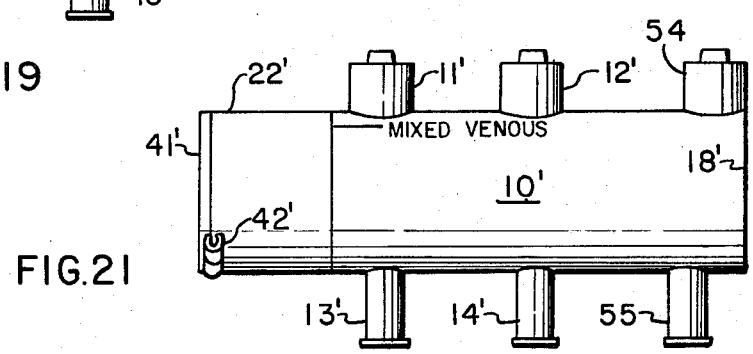
FIG. 21 is a side elevation of the assembled valve, from the side opposite to that shown in FIG. 19.

Referring now to FIG. 19, the surface of the external section 22' of the valve plug is provided with an indicator mark 81. The surface of the housing 10' is provided with several cooperating indicator marks, namely a CARDIAC OUTPUT mark 82, a MIXED VENOUS FLUSH mark 83, an ARTERIAL mark 84, a PROXIMAL/CVP mark 85, and a DISTAL mark 86. Referring to FIG. 21, the other side of the housing 10' is provided with a MIXED VENOUS mark 87. Referring to FIG. 20, the closure cap flap 44' is provided with indicia, "CARDIAC OUTPUT", and the other closure cap flap 45' is provided with indicia, "MIXED VENOUS".

This three channel, eight port valve is particularly intended for use in a medical system where there is a flow-directed, balloon-tipped pulmonary artery catheter having a distal lumen and a proximal lumen, with ports; two infusion devices; a pressure transducer; and an arterial line. With the use of the valve just described, having three primary helical channels and eight ports, this system can be arranged to permit the monitoring of arterial pressure, the monitoring of pulmonary artery pressure, the monitoring of central venous pressure, withdrawal of a mixed venous sample, and, when the catheter is a thermodilution catheter, the measurement of cardiac output, all without disturbing any connection to the patient, through the use of the valve as a switching device.

Ordinarily in such a system the arterial line would be monitored most of the time. The normal arrangement would be that shown in FIG. 22. In this arrangement, the indicator mark 81 on the projecting end 22' of the valve plug is aligned with the ARTERIAL indicator mark 84 on the housing 10'. The arterial line is connected to the male Luer-type port 54, which is aligned with the transversely-extending passageway 64 and its extension groove 65. The arterial line thus communicates through the port 54, the passageway 64, groove 65, and the female Luer-type port 55, which communicates with the pressure transducer. The distal port of the catheter is connected to the port 12', which communicates through the diametrically-extending passageway 26' through the valve plug, and the port 14', with an infusion device. The proximal lumen or port of the catheter is connected through the port 11', the generally diametrically-extending passageway 25', and the port 13', with an infusion device. All other ports and grooves or channels of the valve plug are occluded.

In this arrangement, the arterial line is thus in communication with the pressure transducer, to permit the arterial pressure to be monitored.

Figure 22:
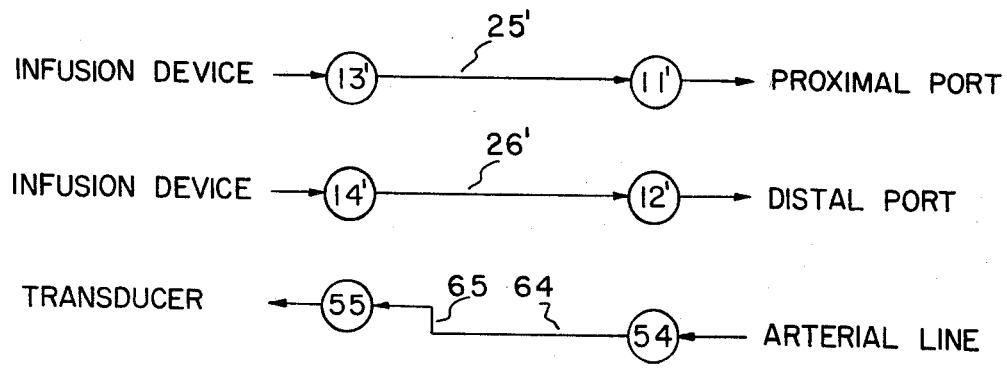
FIGS. 22-31 inclusive are schematic diagrams showing the communications established by the valve in a medical system in which the valve can be used, generally in conjunction with a flow-directed, balloon-tipped pulmonary artery catheter, except for FIGS. 27 and 28, and specifically FIG. 22 indicates use of the valve in a medical system including a flow-directed intravenous catheter having a distal lumen and a proximal lumen, a pressure transducer with a continuous flush device, and two infusion devices, together with an arterial line, the arrangement shown permitting use of the system to monitor arterial blood pressure.
Figure 23:
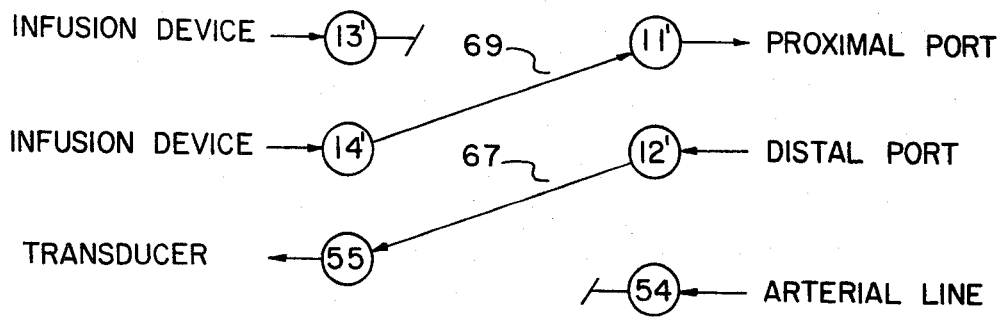

In order to monitor the distal port of the thermodilution catheter for pulmonary artery pressure, the valve plug is rotated 90° from the FIG. 22 position, just described, so that the indicator mark 81 on the valve plug is aligned with the DISTAL mark 86 on the housing. Then, as shown in FIG. 23, the port 54 is occluded. The port 54 communicates with the arterial line and its occlusion prevents any high pressure bleed-back into the valve. The distal port of the catheter is connected to the port 12' and communicates through the helical channel 67 and the port 55 with the pressure transducer. The proximal port of the catheter communicates through the port 11', the helical channel 69, and the port 14', with an infusion device. All other grooves and ports on the valve plug are occluded, as are the ports 54 and 13' of the housing. When the measurements have been completed, the valve plug can be returned to its initial (FIG. 22) position, with the indicator mark 81 on the valve plug aligned with the ARTERIAL mark 84 on the housing, so that the arterial line pressure can be monitored. In situations where there is no arterial line, the valve plug can be left in the position shown in FIG. 23, where the indicator line 81 on the valve plug is aligned with the DISTAL mark 86 on the housing.

Figure 24:
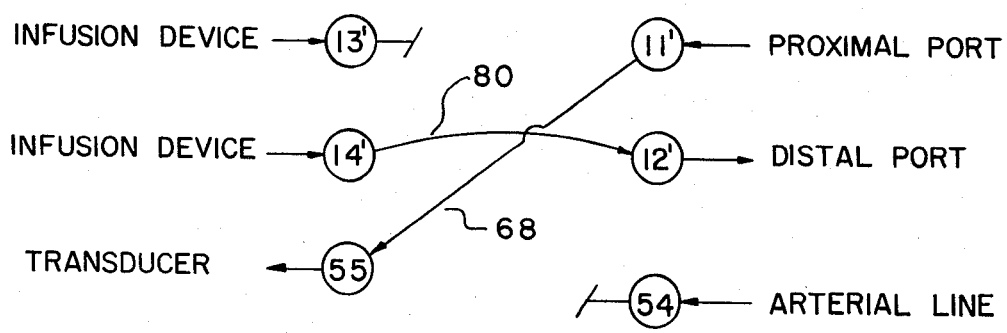

To monitor the proximal port of the catheter for central venous pressure, the valve plug is rotated within the housing until the indicator mark 81 is aligned with the PROXIMAL/CVP mark 85. As shown in FIG. 24, this again occludes the port 54 attached to the arterial line, preventing high pressure bleed-back into the valve. In this arrangement, the proximal port of the catheter is connected to the pressure transducer through the port 11', the helical channel 68, and the port 55. The distal port communicates through the port 12', the curved channel 80, and the port 14', with an infusion device. All of the other ports and channels are occluded. When measurements have been completed, the valve plug can be returned to its normal (FIG. 22) position, that is, with the indicator mark 81 on the valve plug aligned with the ARTERIAL mark 84.

Figure 25:
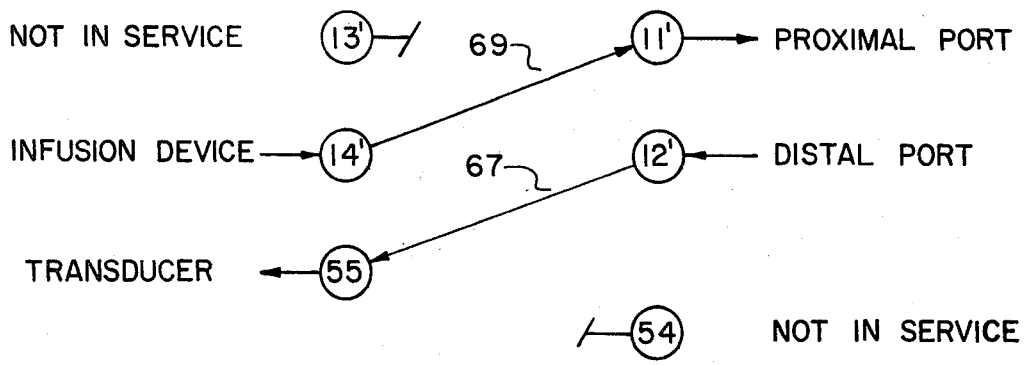
Figure 26:
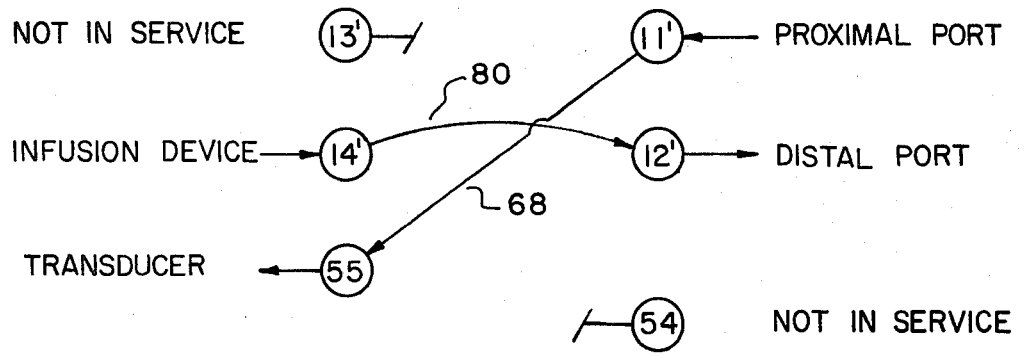

This type of rotary valve can also be used in a slightly different medical system where a flow-directed, balloon-tipped catheter is used without an arterial line. In this configuration, the indicator mark 81 is aligned with the DISTAL mark 86 on the housing. As shown in FIG. 25, this occludes the port 54 which is not in use. In this arrangement, the distal port of the catheter is connected to the pressure transducer through the port 12', the helical channel 67, and the port 55. The proximal port communicates through the port 11', the helical channel 69 and the port 14', with an infusion device. All other ports and channels are occluded. When it is desired to monitor the central venous pressure, the valve plug is rotated until the indicator mark 81 is aligned to the PROXIMAL/CVP mark 85. As shown in FIG. 26, in this arrangement, the proximal port of the catheter is connected to the pressure transducer through the port 11', the helical channel 68, and the port 55. The distal port communicates through the port 12', the curved channel 80, and the port 14', with an infusion device. All other ports and channels are occluded. When measurements have been completed, the valve plug can be returned to its normal (FIG. 24) position for this configuration with the indicator mark 81 on the valve plug aligned with the DISTAL mark 86.

Figure 27:
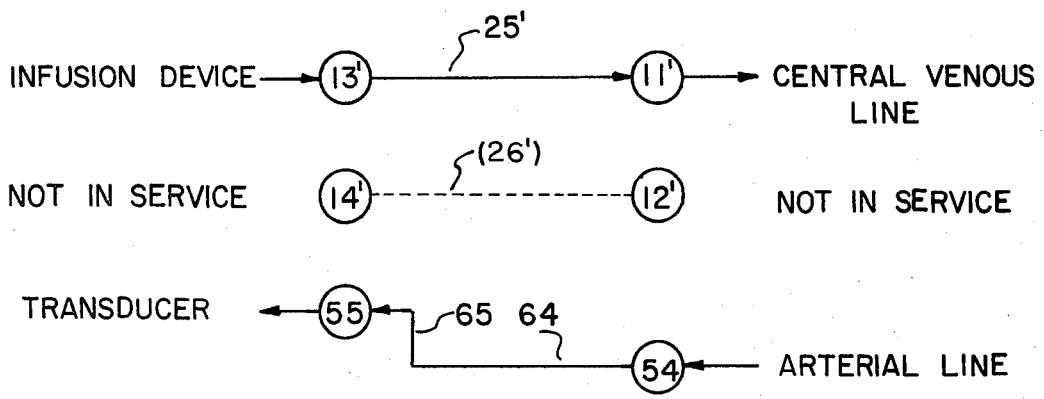

This type of rotary valve can also be used in a slightly different medical system. As shown in FIG. 27, the port 11' can be connected to a CENTRAL VENOUS PRESSURE monitor line, and the port 54 can be connected to an arterial line. With the rotary plug adjusted so that the indicator mark 81 on the valve plug is aligned with the ARTERIAL indicator line 84, the infusion device is connected to the port 13', and there is communication through this port with the diametrically extending passageway 25' and the port 11', to permit infusion of the central venous pressure line. The arterial line is connected to the port 54 and communicates through it with the diametrically extending passageway 64, the groove 65, and the port 55, thus placing the arterial line in communication with the pressure transducer to permit monitoring of arterial pressure. The port 14' and the port 12' communicate through the diametrically-extending passageway 26', but both of these ports are out of service.

Figure 28:
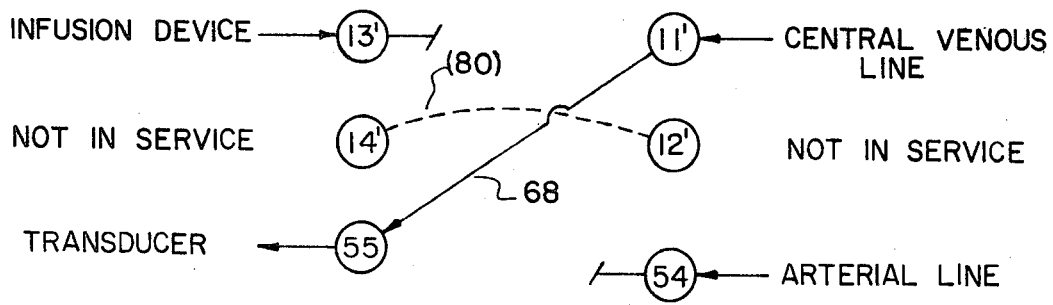

To measure the central venous pressure with this particular medical system, the valve plug is rotated within the housing until the indicator mark 81 on the plug is aligned with the PROXIMAL/CVP mark 85 on the housing. In this orientation, as shown in FIG. 28, the central venous pressure line communicates with the port 11', through the helical channel 68, and the port 55, with the pressure transducer. This permits measurement of the central venous pressure. The arterial line is occluded, as are all other ports and channels, except the curved channel 80 which interconnects the ports 12' and 14', which in any case are not in service.

After the central venous pressure has been measured, the valve plug is rotated to return it to its normal (FIG. 27) position for this particular medical system, with the indicator mark 81 on the valve plug aligned with the ARTERIAL indicator mark 84 on the housing.

Figure 29:
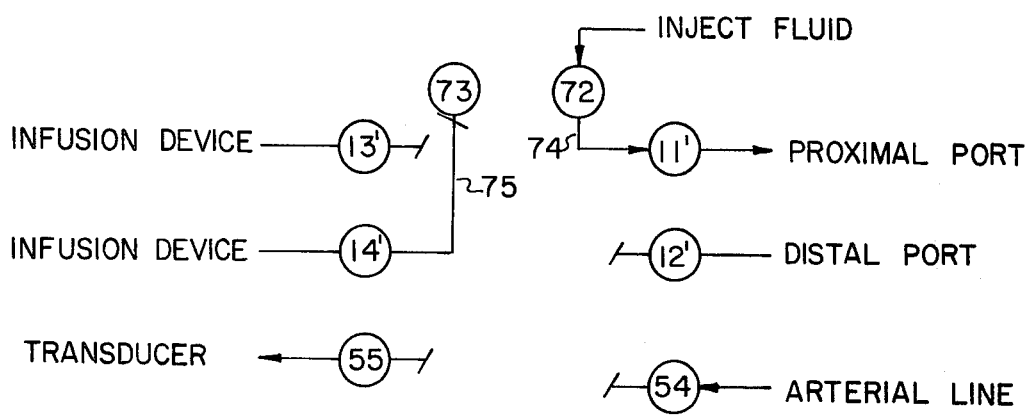

When this particular embodiment of the valve of the invention is employed in a medical system including a thermodilution catheter, some features and advantages arising through the use of the valve can be illustrated by reference to FIG. 29, which illustrates the measurement of cardiac output. For this purpose the indicator mark 81 on the valve plug is aligned with the CARDIAC OUTPUT indicator mark 82 on the housing. Then, as shown in FIG. 29, the proximal port of the catheter communicates through the port 11' of the housing, the port 71, and the axially-extending passageway 74 in the valve plug, with the port 72 in the outer face 34' of the valve plug. The closure cap flap 44' is then lifted off the outer face 34' of the valve plug, removing the closure plug 46' from the port 72. The necessary injection can then be made through the port 72 into the axially-extending passageway 74, for passage through the ports 71 and 11' into the proximal port of the catheter. All other ports and helical channels are occluded. When the injection has been completed, the cap can be cleaned and snapped back into place, to close off the port 72 in sterile fashion.

The valve plug can then be returned to its normal (FIG. 22) position for this medical system, which is the position in which the indicator mark 81 of the valve plug is aligned with the ARTERIAL indicator mark 84 on the housing.

Figure 30:
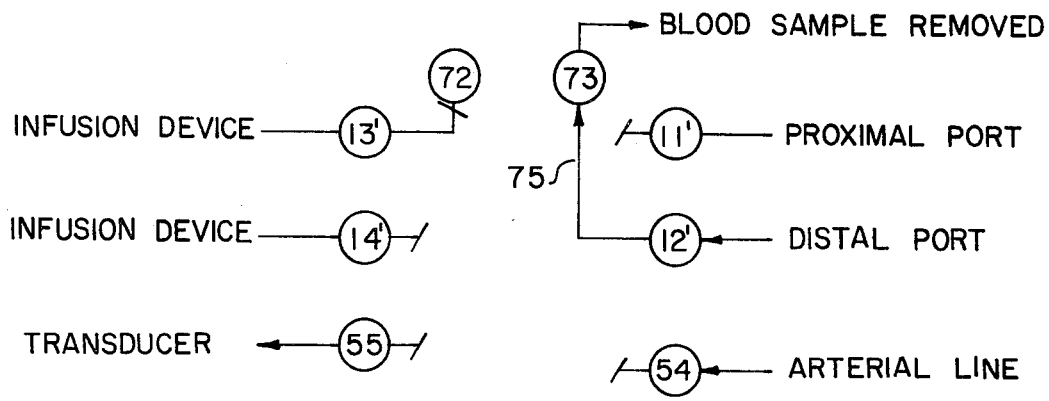

With this same medical system, when it is desired to draw a mixed venous sample from the distal port of the thermodilution catheter, the valve plug is rotated until the indicator mark 81 is aligned with the MIXED VENOUS mark 87 (FIGS. 21 and 30).

Referring now to FIG. 30, in this orientation of the valve, the distal port of the catheter is connected to the port 12', which establishes communication through the port 70 in the cylindrical face of the valve plug with the axially-extending passageway 75 and the port 73 in the outer face 34' of the plug. To take a sample of blood, the closure cap flap 45' is lifted to remove the closure plug 48' from the port 73, and using a syringe, blood from the distal port of the thermodilution catheter can be aspirated from the port 73.

Figure 31:
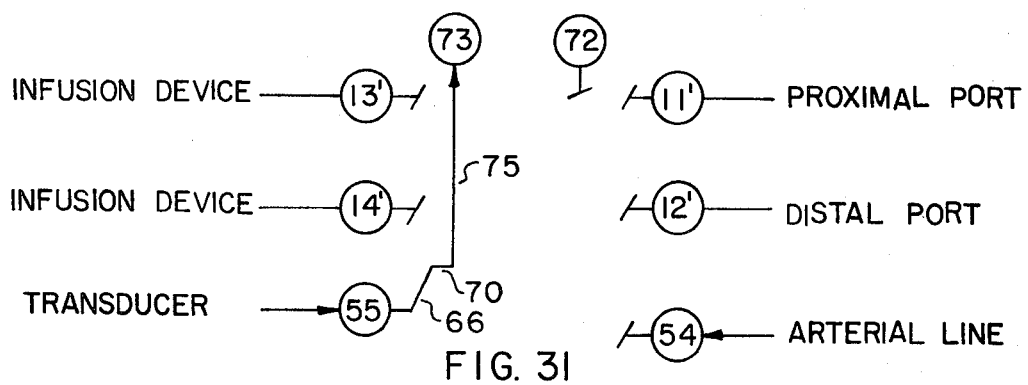

To clear blood from the valve, the valve plug is rotated to align the indicator mark 81 on the valve plug with the MIXED VENOUS FLUSH indicator mark 83. Then, as shown in FIG. 31, communication is established from the port 73 through the axially-extending passageway 75, and through the port 70, with the helical groove 66 which in turn communicates through the housing port 55 with the pressure transducer. Flushing originates at the transducer, with the flush liquid traveling through the communicating ports and passageways just mentioned. When the flushing has been completed, the closure cap flap 45' is cleaned and snapped back in place, and the valve plug may be returned to its normal position.

Advantages of This Embodiment of the Invention

Generally this embodiment of the invention affords all of the advantages already mentioned for the two channel, six port valve embodiment. However, in addition, the three channel, eight port embodiment is much more flexible, so that the valve can be used in several different modes. That is, it can be used in a medical system including a thermodilution catheter with an arterial line; with a thermodilution catheter alone; or with an arterial line in conjunction with a central venous pressure line, all without compromise of the valve function.

In this embodiment of the invention, the offset of the housing port 55 from the opposite port 54 on the other side of the housing has a definite advantage. The port 55 is normally placed in communication with the pressure transducer. The port 54 is normally used for communication with the arterial line. The offset prevents high pressure bleed-back into one of the low pressure input ports.

Still another advantage is that one pressure transducer can be employed for all desired pressure measurements. Simple manual rotation of the plug is the only requirement for switching the transducer among channels.

Concluding Remarks

Two preferred embodiments of the invention have been described in some detail above. The functions that are performed are of particular importance, whereas the specific structure illustrated in the drawings, while preferred, need not necessarily be used to perform the functions. For example, in both embodiments of the invention, the valve plug has been shown as having a generally cylindrical surface, as has the bore of the housing. Other mating surfaces of revolution would perform the same functions. Conical sections, for example, could be used for the mating surfaces of the rotary plug and of the bore of the housing.

In describing the cooperating pairs of ports in the housing, it has been mentioned that they are preferably axially spaced relative to the bore of the housing. However, by appropriate modifications in construction, angular spacing could be employed, with the center lines of all ports falling in the same plane, while still accomplishing the desired functions. Some modification in the plug construction would of course be required. In addition, the spacing between the pairs of ports may be a combination of angular and axial. Those constructions illustrated are those that are preferred and generally those that are the simplest.

Similarly, while diametrically opposed ports, and diametrically extending passageways for communication between ports, are preferred, such an arrangement is not essential.

The valve plug preferably is constructed from a resilient plastic material, as a single part. Polypropylene produces a very strong hinge for the closure cap, although a long life is not essential since in most cases the valve would be constructed to be expendible. In any case, it is preferred for medical applications that the valve plug be opaque, whereas the housing should be transparent, to facilitate inspection for the presence of air bubbles, and to permit visual inspection of fluid flow. The valve can thus be made from only two molded parts, which preferably are sterilizable. However, the valve is intended for general utility and is especially useful wherever a cross-over between two parallel fluid flow lines is necessary.

While the invention has been disclosed herein by reference to the details of preferred embodiments thereof, it is to be understood that such disclosure is intended in an illustrative, rather than in a limiting sense, and it is contemplated that various modifications in the construction and arrangement of the parts will readily occur to those skilled in the art, within the spirit of the invention and the scope of the appended claims.

What is claimed is:
1. A rotary valve comprising
    a housing having a bore extending partly therethrough that is bounded by a surface of revolution that is defined by the side wall of the housing, said housing having a plurality of ports opening into its bore through the side wall of the housing, said ports being disposed in cooperating pairs, each pair being spaced from each other pair, and
    a valve plug movably mounted in said bore for rotary movement therein, and having at least one channel in the surface thereof that confronts said surface of revolution of the housing, said channel being disposed, upon proper orientation of the plug in the housing by relative rotation thereof, each to be in communication with one port of one pair of ports and another port from another pair of ports, respectively, to place said last-named ports in communication with each other,
    said valve plug also being formed with additional passageways therein that each extend partially axially through the plug and partially transversely therethrough respectively, one said transversely extending passageway portion being disposed in axial alignment with one of said pairs of housing ports, and one other said transversely extending passageway portion being disposed in axial alignment with one other of said pairs of housing ports, said transversely-extending passageway portions being positioned respectively so that upon proper orientation of the plug in the housing by relative rotation thereof, a single one of said transversely-extending passageway portions can be placed in communication with one of said housing ports in a first of said pairs of ports, and the other of said transversely extending passsageway portions and the remaining housing ports are either sealed closed by the surface of the plug or the said other of said transversely extending passageway portions is placed in communication with one of said housiing ports in a second of said pairs of ports.

2. The rotary valve of claim 1 comprising separate, readily releasable means for sealing closed each said axially-extending passageway at or adjacent an outer face of the valve plug.

3. The rotary valve of claim 2 wherein said housing is formed with means permitting readily detachable securing of tubing to each said housing port.

4. The rotary valve of claim 3 wherein the valve is for medical use and all parts thereof are readily sterilizable.

5. The valve of claim 4 wherein the housing is transparent and the valve plug is opaque.

6. The rotary valve of claim 1, 2, 3, 4 or 5 wherein said valve plug is also formed with at least one transversely-extending passageway therein that is disposed, upon proper orientation of the plug in the housing by relative rotation thereof, to be in communication with one port of one of said pairs of ports and the other port from the same pair of ports, respectively, to place said last-named ports in communication with each other.

7. The rotary valve of claim 6 wherein said ports are axially spaced relative to said bore, said plug is formed with a plurality of transversely-extending passageways, and transversely extending passageways comprise one transversely-extending passageway for each said pair of ports respectively.

8. A rotary valve comprising a housing having a bore extending partly therethrough that is bounded by a surface of revolution, said housing having a plurality of ports opening into its bore through the side wall of the housing, said ports being disposed in cooperating pairs, each pair being spaced from each other pair, and a valve plug movably mounted in said bore for rotary movement therein, and having passageways therein, said passageways being positioned in one orientation of said plug to be in communication with said pairs of ports respectively to place each port in communication with the other, cooperating member of its pair, said valve plug also being formed with other passageways therein that are disposed, upon proper orientation of the plug in the housing by relative rotation thereof, each to be in communication with one port of one pair and another port from another pair, respectively, to place said last-named ports in communication with each other, wherein said ports are axially spaced relative to said bore, said passageways comprise one passageway for each said pair of ports and are formed to extend transversely through said valve plug respectively, said plug being formed with a surface thereof that confronts and engages the surface of the bore of the housing, said plug being formed in its said surface with a plurality of channels, said channels providing respectively said other passageways that can provide communication between one port of one pair and another port from another pair, wherein there are two of said pairs of ports, two of said transversely-extending passageways, and two of said channels, and wherein said plug is formed with an outer face and with another passageway that extends partly axially through said plug from said outer face and partly transversely of said plug, said transversely-extending passageway portion being positioned so that upon proper orientation of said plug in the housing by relative rotation thereof, the transversely extending passageway portion is placed in communication with one of said housing ports and the remaining housing ports are sealed closed by the surface of said plug.

9. The rotary valve of claim 8 comprising readily releasable means for sealing closed said axially-extending passageway at or adjacent said outer face of the valve plug.

10. The rotary valve of claim 8 wherein said plug is formed with two additional passageways that each extend partially axially through the plug and partially transversely thereof respectively, one said transversely extending passageway portion being disposed in axial alignment with one of said pairs of housing ports, and the other said transversely extending passageway portion being disposed in axial alignment with the other of said pairs of housing ports, said transversely-extending passageway portions being positioned respectively so that upon proper orientation of the plug in the housing by relative rotation thereof, a single one of said transversely-extending passageway portions can be placed in communication with one of said housing ports, and the other of said transversely extending passageway portions and the remaining housing ports are sealed closed by the surface of said plug.

11. The rotary valve of claim 10 comprising separate, readily releasable means for sealing closed each said axially-extending passageway at or adjacent said outer face of the valve plug.

12. The rotary valve of claim 11 wherein said housing is formed with means permitting readily detachable securing of tubing to each said housing port.

13. The rotary valve of claim 12 wherein the valve is for medical use and all parts thereof are readily sterilizable.

14. The valve of claim 13 wherein the housing is transparent and the valve plug is opaque.

15. A rotary valve comprising a generally cup-shaped housing that has a generally cylindrical bore, said housing being formed so that said bore is open at one of its ends and closed at its opposite end, said housing having a plurality of ports opening into its bore, said ports being disposed in cooperating pairs, each said pair of ports being spaced axially of said bore from each other said pair of ports, and a valve plug that is engageable in said bore and that has a generally cylindrical surface that confronts and engages against the surface of the bore in substantially fluid-tight relation, said valve plug being rotatable in said bore, said plug being formed with passageways extending transversely thereof and corresponding in number to the number of said pairs of ports, said passageways being spaced from each other axially of said bore by a distance corresponding to the axial distance between the ports in said pairs of ports, said passageways being positioned, in one orientation of said plug, to be in communication with said pairs of ports respectively to place each port in communication with the other, cooperating member of its pair, said plug also being formed with means to limit the extent of its insertion into said bore so as to cause the said passageways to be positionable, upon proper orientation of the plug, in alignment with said ports respectively, and said valve plug also being formed with other passageways therein that are disposed, upon orientation of the plug in the housing, each to be in communication with one port of one pair and another port from another pair, respectively, to place said last named ports in communication with each other, wherein there are two of said pairs of said ports, two of said transversely extending passageways, and two of said channels formed in the surface of said plug, wherein the ports of each said pair of ports are diametrically opposed to each other, and said transversely extending passageways are disposed to extend diametrically of said plug, wherein said other passageways are channels formed in the generally cylindrical surface of said plug, and wherein said plug is formed with an outer face and with an additional passageway that extends partly axially therethrough from said outer face and partly transversely thereof, said transverse portion being positioned so that upon proper orientation of said plug it is placed in communication with one of said housing ports and the remaining housing ports are sealed closed by the surface of said plug.

16. The rotary valve of claim 15 comprising releasable means for sealing closed said axially-extending passageway.

17. The rotary valve of claim 15 wherein said valve plug is formed with two additional passageways that each extend partly axially therethrough and partly transversely thereof, one of said transversely extending passageways being disposed in axial alignment with one of said pairs of ports, and the other of said transversely extending passageways being disposed in axial alignment with the other of said pairs of ports.

18. The rotary valve of claim 17 comprising separate, releasable means for sealing closed each of said axially extending passageways.

19. The rotary valve of claim 15 wherein said plug is formed with an outer face and with an additional passageway that extends partly axially therethrough from said outer face and partly transversely thereof, said transverse portion being positioned so that upon proper orientation of said plug it is placed in communication with one of said housing ports and the remaining housing ports are sealed closed by the surface of said plug.

20. The rotary valve of claim 19 comprising releasable means for sealing closed said axially-extending passageway.

21. The rotary valve of claim 17 or 19 wherein said housing is formed with means permitting readily detachable securing of tubing to each said housing port.

22. The rotary valve of claim 16 wherein said housing is formed with means permitting readily detachable securing of tubing to each said housing port.

23. The rotary valve of claim 21 wherein said valve is formed for medical use from readily sterilizable parts.

24. The valve of claim 23 wherein said housing is transparent and the male plug is opaque.

25. A medical system comprising the rotary valve of claim 17 or 18 for connection in a system including an intravenous catheter having a distal lumen and a proximal lumen, a pressure transducer with a continuous flush device, and an infusion device, wherein, when said plug is oriented to place the valve plug in position to close off all of said ports, it may be further oriented to place one of said additional passageways in communication with the port that is in communication with said pressure transducer with a continuous flush device, while continuing to close off the remaining ports.

26. A medical system comprising the rotary valve of claim 17 or 18 for connection in a system including an intravenous catheter having a distal lumen and a proximal lumen, a pressure transducer with a continuous flush device, and an infusion device, wherein when the plug is oriented so that the plug closes off all of said ports, it may be further oriented to place one of said additional passageways in communication with the port communicating with the distal lumen, while continuing to close off the remaining ports.

27. A rotary valve comprising
   a housing having a bore extending partly therethrough that is bounded by a surface of revolution that is defined by the side wall of the housing, said housing having a plurality of ports opening into its bore through the side wall of the housing, said ports being disposed in cooperating pairs, each pair being spaced from each other pair, and
   a valve plug movably mounted in said bore for rotary movement therein, and having transversely-extending passageways therein, said passageways being positioned in one orientation of said plug to be in communication with said pairs of ports respectively to place each port in communication with the other, cooperating member of its pair,
   said valve plug also being formed with additional passageways therein that each extend partially axially through the plug and partially transversely therethrough respectively, one said transversely extending passageway portion being disposed in axial alignment with one of said pairs of housing ports, and one other said transversely extending passageway portion being disposed in axial alignment with one other of said pairs of housing ports, said transversely-extending passageway portions being positioned respectively so that upon proper orientation of the plug in the housing by relative rotation thereof, a single one of said transversely-extending passageway portions can be placed in communication with one of said housing ports, and the other of said transversely extending passageway portions and the remaining housing ports are sealed closed by the surface of said plug,
   said rotary valve further comprising separate, readily releasable means for sealing closed each said axially-extending passageway at or adjacent said outer face of the valve plug, and
   wherein said valve plug is also formed with other passageways therein that are disposed, upon proper orientation of the plug in the housing by relative rotation thereof, each to be in communication with one port of one of said pairs of ports and another port from another of said pairs of ports, respectively, to place said last-named ports in commumication with each other.

28. The rotary valve of claim 27 wherein said ports are axially spaced relative to said bore, said transversely extending passageways comprise one passageway for each said pair of ports respectively, said plug being formed with a surface thereof that confronts and engages the surface of the bore of the housing, said plug being formed in its said surface with a plurality of channels, said channels providing respectively said other passageways that can provide communication between one port of one of said pairs of ports and another port from another of said pairs of ports.

29. The rotary valve of claim 28 wherein said housing is formed with means permitting readily detachable securing of tubing to each said housing port.

30. The rotary valve of claim 29 wherein the valve is for medical use and all parts thereof are readily sterilizable.

31. The valve of claim 30 wherein the housing is transparent and the valve plug is opaque.

* * * * *